(12) United States Patent
Curti et al.

(10) Patent No.: US 6,655,385 B1
(45) Date of Patent: Dec. 2, 2003

(54) NASAL CANNULA

(75) Inventors: James N. Curti, Bakersfield, CA (US); James Chua, Bakersfield, CA (US); Peter W. Salter, Tehachapi, CA (US)

(73) Assignee: Salter Labs, Arvin, CA (US)

( * ) Notice: Subject to any disclaimer, the term of this patent is extended or adjusted under 35 U.S.C. 154(b) by 153 days.

(21) Appl. No.: 09/837,720

(22) Filed: Apr. 18, 2001

Related U.S. Application Data

(62) Division of application No. 09/184,111, filed on Nov. 2, 1998, which is a continuation of application No. PCT/US98/05573, filed on Apr. 3, 1998.

(51) Int. Cl.⁷ .......................... A61M 15/08; A62B 7/00

(52) U.S. Cl. .......................... 128/207.18; 128/203.22; 128/204.18; 128/206.11; 128/912

(58) Field of Search ................ 128/204.18, 204.22, 128/207.18, 912, 203.22, 203.29, 204.26, 206.11, 207.17, 207.16; 600/531, 532, 538

(56) References Cited

U.S. PATENT DOCUMENTS

| | | |
|---|---|---|
| 5,046,491 A | 9/1991 | Derrick |
| 5,137,017 A | 8/1992 | Salter |
| 5,335,656 A | 8/1994 | Bowe et al. |
| 5,626,131 A | 5/1997 | Chua et al. |
| 5,682,881 A | 11/1997 | Winthrop et al. |

FOREIGN PATENT DOCUMENTS

WO    WO 89/09565    * 10/1989

* cited by examiner

*Primary Examiner*—Weilun Lo
*Assistant Examiner*—Darwin P. Erezo
(74) *Attorney, Agent, or Firm*—Davis & Bujokd, P.L.L.C.

(57) ABSTRACT

A nasal cannula for insufflating a patient with oxygen through one nare of the cannula and separately analyzing the exhaled gases from the patient by drawing the sampling of the exhaled gas from the other nare of the cannula into a conventional carbon dioxide analyzer. A further addition of holes or vents in the nares of the cannula are provided on both the interior and posterior of one or both nares in order to substantially reduce or eliminate the incidence of occlusion of the tip of the carbon dioxide sampling nare.

8 Claims, 1 Drawing Sheet

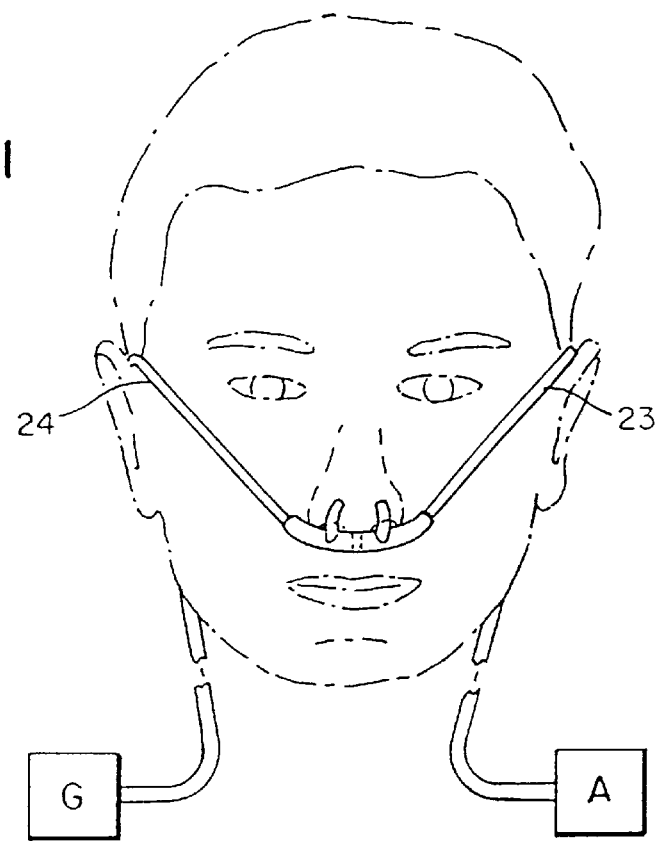
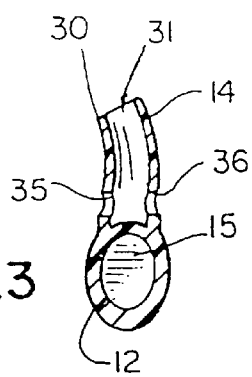
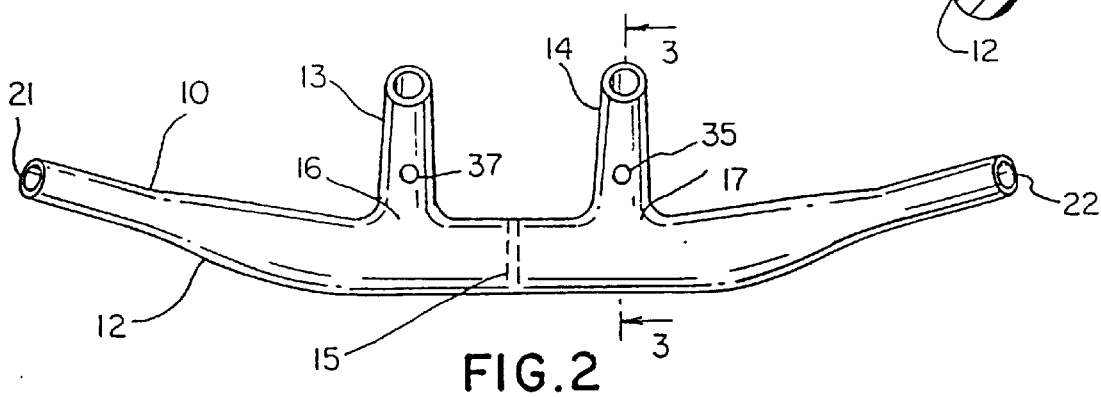
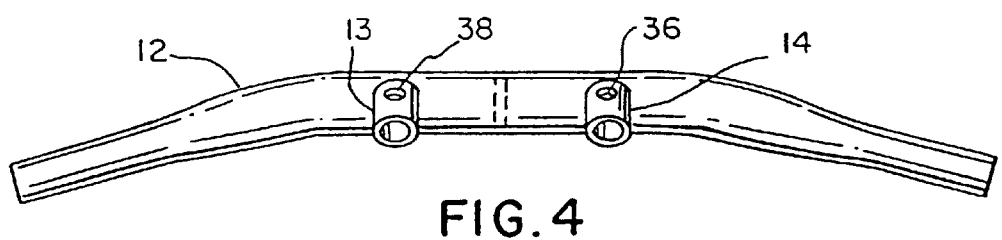

NASAL CANNULA

This is a divisional of U.S. patent application Ser. No. 09/184,111 filed Nov. 2, 1998 which is a continuation of International Application PCT/US98/05573, filed Apr. 3, 1998.

BACKGROUND OF THE INVENTION

The practice of measuring end-tidal carbon dioxide during the administration of anesthesia, particularly regional anesthesia, has grown markedly in the past several years. The reasons that anesthesiologists have embraced this technique are described more fully in U.S. Pat. No. 5,335,656 which is incorporated herein by reference in its entirety.

The preferred nasal cannula used in this procedure is a cannula which insufflates the patient with oxygen through one nare of a cannula and separately samples the exhaled gases by drawing the exhaled gas from the other nare into a conventional carbon dioxide analyzer. The cannula is preferably provided with an internal wall or system in the face piece to keep the conduits separate for insufflation and sampling, however, separate lines can be used or even multiple nares for insufflation and sampling, though the latter device substantially increases the risk of gases mixing which can distort the readings for end-tidal carbon dioxide. It is preferred that two nares only are employed and that each nare performs only one function, i.e., insufflation or sampling into or from separate nostrils. Likewise, insufflation has normally been continuous, however, it could advantageously be intermittent which would further improve the end-tidal carbon dioxide measurement by insuring that gases being sampled were representative of exhaled gases undiluted by the other gases being insufflated. Most preferably, the intermittent insufflation is accomplished by the apparatus and method described in U.S. Pat. No. 5,626,131 which is incorporated herein by reference in its entirety. Other so-called demand insufflation devices which begin insufflation upon the start of inhalation can also be employed.

Normal nasal cannulae are designed with the nares having a slight inward curvature as they extend upward from the face piece. This is anatomically desirable and important for imparting the proper direction of insufflating gas into the nasal cavities. When the patient is in the upright sitting position or ambulatory, this is the most satisfactory design configuration. Conversely, problems can be encountered if the patient is horizontal or prone and tends to accumulate secretions in the nasal cavities. It can be a particularly vexing problem if either the insufflation or sampling nare becomes occluded during the use of the cannula for sampling and monitoring end-tidal carbon dioxide during the administration of anesthesia.

OBJECTS OF THE INVENTION

It is therefore an object of the present invention to provide a nasal cannula structure for sampling carbon dioxide which reduces or eliminates the incidence of occlusion of the tip of the carbon dioxide sampling nare during the removal of carbon dioxide by the sampling line connected to a monitoring device and/or a source of suction or vacuum.

It is also an object of the present invention to provide a nasal cannula for insufflating a patient with oxygen while accurately monitoring end-tidal carbon dioxide, that will continue to function properly for its intended purpose when either or both nares become occluded for any reason.

It is a further object to accomplish the foregoing objects with a minimum risk of distorting the end-tidal carbon dioxide readings from the sampled exhalation gases during the administration of anesthesia.

BRIEF SUMMARY OF THE INVENTION

The foregoing objects and advantages are obtained by providing a nasal cannula structure that is adapted for insufflation and sampling, with additional holes or vents on the nares of the nasal cannula, preferably both anterior and posterior of one or both nares at a location proximate the entrance of the nasal passageways when the cannula is in use.

BRIEF DESCRIPTION OF THE DRAWINGS

FIG. 1 is a frontal view of a normally positioned nasal cannula on a patient (shown in phantom) connected to a gas source (G) and a gas analyzer (A).

FIG. 2 is a rear view of the cannulae face piece shown in FIG. 1.

FIG. 3 is a partial cross section of a nare of the nasal cannula taken along the lines and arrows 3—3 of FIG. 2.

FIG. 4 is a plan view of the nasal cannula of FIG. 2.

DETAILED DESCRIPTION OF THE ILLUSTRATED EMBODIMENT

The nasal cannula 10 of one embodiment of the present invention consists of a generally tubular face piece 12 having two nares 13 and 14 and a septum 15 disposed in the center of the face piece 12 between the openings 16 and 17, respectively, of the nares 13 and 14 (see FIGS. 2, 3 and 4). The openings 21 and 22 on the ends of the face piece 12 are affixed to separate tubes 23 and 24 as shown in FIG. 1, which are separately connected to a source of insufflating gas (G), such as oxygen, and a commercial carbon dioxide monitoring unit (shown as A) which, in turn, has or is connected to a vacuum pump or other means for drawing exhaled breath containing carbon dioxide into an instrument that is capable of measuring the concentration of the carbon dioxide in the sampled gas.

During use of the cannula for both insufflation and the monitoring of carbon dioxide concentration in the exhaled breath (depicted schematically in FIG. 1), the readings for end-tidal carbon dioxide can become distorted where there is undesirable mixing with room air or with excess insufflating gas. Likewise, carbon dioxide measuring devices which typically employ varying amounts of suction or vacuum to obtain the gas sample to be analyzed, can unduly dilute the sample or more seriously can draw the tip 30 of the sampling nare (representatively shown in FIG. 3) onto the adjacent surface of the tissue of the nasal passage and occlude the opening 31 thereby restricting or even preventing sampling of the exhaled gases for their carbon dioxide concentration.

This is an especially serious problem where the patient is prone and secretions can be present which are drawn into the opening 31 at the tip 30 and which then either partially or totally occlude the opening 31, during the administration of anesthesia.

The anesthesiologist must respond by clearing the nare opening after first removing the cannula from its location on the face of the patient. This may be complicated where the patient is draped in a manner which covers the cannula, such as in eye surgery. It may also be difficult to detect the occlusion where the end-tidal carbon dioxide measurement signal is only partially degraded.

It has been discovered that the expedient of additionally providing the nares with very small holes, shown collectively at 35 and 36 and 37 and 38, achieves the desired result of preventing an undesirable and unnecessary level of suction at the opening 31 of the tip 30 from developing sufficiently to draw the opening 31 into the nasal tissue thereby occluding the opening. The holes are sized large enough to prevent sufficient suction from developing at the tip 30 to draw in mucosal secretions or attach the tip by suction to the soft mucosal tissue, while still drawing an undiluted sample of the exhaled gases to provide good end-tidal carbon dioxide measurements. Likewise, too large an opening for these holes would undesirably dilute the exhaled gas sample with room air or excess insufflation gas.

Most preferably, as previously noted, the nasal cannula of the present invention can be used in combination with an oxygen delivery system that delivers the insufflating gas intermittently. The delivery can be initiated at any time after the peak end-tidal carbon dioxide measurement is achieved during exhalation and continuing into the inhalation phase of the breathing cycle or could be inhalation activated or designed to deliver only during selected portions of all or only some of the inhalation phases of a patient's breathing cycles. Preferably, the delivery should begin before the termination of the exhalation phase, such as is described in U.S. Pat. No. 5,626,131. Using intermittent delivery substantially reduces the possibility of distorted carbon dioxide readings due to gas mixing.

Likewise, slits or slots (not shown) may be employed in the nares which could function in the same manner as the holes described if they are positioned in such a manner to avoid collapse or occlusion with the nasal tissues and provide the desired function of preventing sufficient suction from developing at the tip of the nare to cause it to be drawn, by suction, onto the tissues. The holes provided as described herein are preferred as there is less risk of occlusion and trauma from the edges of slits or slots to the nasal tissue and potentially there is less risk of gas dilution and mixing from occurring where the slits or slots are overly large.

Further, the combination of intermittent insufflation using the cannula of the present invention produces the desired end-tidal carbon dioxide measurement, as described, and helps prevent patient desaturation during the rigors of surgery and anesthesia administration.

Preferably, the size of the openings is from between about 0.05 to about 0.07 inches though larger or smaller holes or single holes may be advantageously employed in combination with specific analytical apparatuses. The size and location of the openings can vary with the analyzer selected and the proper function confirmed without undue experimentation.

The invention described herein is to be limited only by the scope of the appended claims and the applicable prior art.

What is claimed is:

1. A method of preventing the occlusion of a nasal cannula for insufflating a treating gas into a nose of a patient and measuring carbon dioxide content in the exhalation of the patient, said method comprising the steps of:

forming an elongated hollow body including a tubular portion adapted to be received on the skin surface adjacent the nose;

providing a wall within said hollow body defining therein both an inhalation manifold and an exhalation manifold, each manifold having a single gas entrance communicating with a single gas exit, said wall providing a gas-tight seal positively preventing fluid communication between said inhalation and exhalation manifolds;

forming a first hollow prong having a fixed length separating a first attached end opening in fluid communication with said single gas exit of said inhalation manifold, and adapting a first free end opening to be received in a first nasal passage of the nose for insufflating said treating gas into the nose;

forming a second hollow prong having a fixed length separating a second attached end opening in fluid communication with said single gas entrance of said exhalation manifold, and adapting a second free end opening to be received in a second nasal passage of the nose for withdrawing a portion of the exhalation therefrom;

connecting said single gas entrance of said inhalation manifold to a supply of treating gas and insufflating said treating gas into the nose;

connecting said single gas exit of said exhalation manifold with a carbon dioxide measuring device and withdrawing an exhaled gas sample from said exhalation manifold and measuring the concentration of carbon dioxide in the exhaled gas sample;

providing at least said second prong with an additional opening communicating with the hollow interior of said second prong and said exhalation manifold; and sizing the additional opening large enough to prevent sufficient suction developing at the tip to draw in mucosal secretions or attach the tip by suction to the mucosal tissue, and small enough to prevent dilution of the exhaled gas sample by ambient air or excess insufflation gas.

2. The method of preventing the occlusion of a nasal cannula as set forth in claim 1 wherein the additional opening in said second prong is between about 0.05 to 0.07 inches in diameter.

3. The method of preventing the occlusion of a nasal cannula as set forth in claim 1 wherein a pair of coaxially aligned openings are provided in at least said second prong.

4. The method of preventing the occlusion of a nasal cannula as set forth in claim 2 further comprising the step of locating the additional opening in said second prong proximate the second attached end and substantially adjacent the manifold gas exit.

5. The method of preventing the occlusion of a nasal cannula as set forth in claim 4 further comprising the step of reducing the possibility of distorted carbon dioxide readings due to a diluted gas sample by delivering the insufflating gas intermittently.

6. The method of preventing the occlusion of a nasal cannula as set forth in claim 5 wherein delivery of the intermittent insufflating gas is initiated at any time after the peak end-tidal carbon dioxide measurement is achieved during exhalation and continuing into the inhalation phase of the breathing cycle.

7. The method for monitoring end tidal $CO_2$ in unintubated, conscious, spontaneously breathing patients who are receiving administration of local and regional anesthesia or during recovery from residual general anesthesia consisting of the steps of:

providing a nasal cannula on a patient, said cannula having an elongated hollow body; a gas-tight partition in said hollow body to divide the hollow body into a first zone and a second zone;

separating said first and second zones from each other by said gas tight partition and attaching a gas supply means including first conduit means with said first zone and a source of oxygen, a second conduit means communicating with said second zone and communicating with a means for detecting and measuring the partial pressure of carbon dioxide in the exhaled gases;

providing said elongated hollow body with fixed length separate first and second hollow nasal prongs each communicating by way of an associated opening with one of said first and second zones and respectively with each nostril of the patient;

supplying oxygen to said patient from the source of oxygen through said first conduit means to the first zone of the elongated hollow body and into the patient's nostril through said first nasal prong;

withdrawing exhaled breath containing carbon dioxide from said patient through said second nasal prong into the second zone of said elongated hollow body, through said second conduit means and into said means for detecting and measuring the partial pressure of carbon dioxide; and determining the partial pressure of carbon dioxide at the end of the patient's exhalation to obtain a clinical approximation of the partial pressure of arterial carbon dioxide;

forming in said second hollow nasal prongs at least a second opening in addition to the opening of said nasal prong and sizing said second opening to prevent the withdrawing of exhaled breath from causing occlusion of said second hollow nasal prong by adjacent tissue or patient secretions.

8. A method of preventing the occlusion of a nasal cannula for insufflating a treating gas into a nose of a patient and measuring carbon dioxide content in the exhalation of the patient, said method comprising the steps of:

forming an elongated hollow body including a tubular portion adapted to be received on the skin surface adjacent the nose;

providing a wall within said hollow body defining therein both an inhalation manifold and an exhalation manifold, each manifold having a single gas entrance communicating with a single gas exit, said wall providing a gas-tight seal positively preventing fluid communication between said inhalation and exhalation manifolds;

forming a first hollow prong having a fixed length separating a first attached end opening in fluid communication with said single gas exit of said inhalation manifold, and adapting a first free end opening to be received in a first nasal passage of the nose for insulating said treating gas into the nose;

forming a second hollow prong having a fixed length separating a second attached end opening in fluid communication with said single gas entrance of said exhalation manifold, and adapting a second free end opening to be received in a second nasal passage of the nose for withdrawing a portion of the exhalation therefrom;

connecting said single gas entrance of said inhalation manifold to a supply of treating gas and insufflating said treating gas into the nose;

connecting said single gas exit of said exhalation manifold with a carbon dioxide measuring device and withdrawing an exhaled gas sample from said exhalation manifold and measuring the concentration of carbon dioxide in the exhaled gas sample; and preventing sufficient suction from developing at the second free end opening to draw in mucosal secretions or attach the opening by suction to the mucosal tissue, and to prevent dilution of the exhaled gas sample by ambient air or excess insufflation gas by providing at least said second prong with a pair of coaxially aligned openings between about 0.05 to 0.07 inches in diameter communicating with the hollow interior of said second prong and said exhalation manifold.

* * * * *